United States Patent [19]

Kurono et al.

[11] Patent Number: 5,171,865
[45] Date of Patent: Dec. 15, 1992

[54] PROCESS FOR THE PREPARATION OF OPTICALLY ACTIVE 4-OXO-1-BENZOPYRAN-2-CARBOXYLIC ACID DERIVATIVES AND INTERMEDIATES THEREOF

[75] Inventors: Masayasu Kurono; Yasuaki Kondo; Kenji Miura; Toshinao Usui; Ryoichi Unno; Takuji Kakigami; Kiichi Sawai, all of Nagoya, Japan

[73] Assignee: Sanwa Kagaku Kenkyusho Co., Ltd., Aichi, Japan

[21] Appl. No.: 664,686

[22] Filed: Mar. 5, 1991

Related U.S. Application Data

[62] Division of Ser. No. 315,877, Feb. 27, 1989, abandoned.

[30] Foreign Application Priority Data

Feb. 29, 1988 [JP] Japan ................... 63-44644

[51] Int. Cl.$^5$ ........................... C07D 311/26
[52] U.S. Cl. ................................. 549/402
[58] Field of Search ........................ 549/402

[56] References Cited

U.S. PATENT DOCUMENTS 3,857,856 12/1974 Cairns et al. .................. 549/402
3,862,143 1/1975 Klutchko et al. ............... 549/402

FOREIGN PATENT DOCUMENTS 331078 9/1989 European Pat. Off. ......... 549/402

Primary Examiner—C. Warren Ivy
Assistant Examiner—Raymond Covington
Attorney, Agent, or Firm—Nikaido, Marmelstein, Murray & Oram

[57] ABSTRACT

A process for the preparation of optically active 4-oxo-1-benzopyran-2-carboxylic acid derivatives of the formula

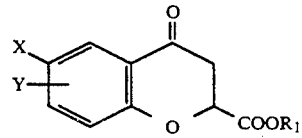

wherein X and Y are hydrogen atom, halogen atom or alkyl group, and
$R_1$ is hydrogen atom or alkyl group,
intermediates thereof, as well as a process for the preparation of the intermediates.

2 Claims, No Drawings

PROCESS FOR THE PREPARATION OF OPTICALLY ACTIVE 4-OXO-1-BENZOPYRAN-2-CARBOXYLIC ACID DERIVATIVES AND INTERMEDIATES THEREOF

This is a division of application Ser. No. 315,877 filed Feb. 27, 1989 now abandoned.

BACKGROUND OF THE INVENTION

1. Field of the Invention

The present invention relates to a process for the preparation of 4-oxo-1-benzopyran-2-carboxylic acid derivatives, intermediates for synthesizing the compounds, and a process for the preparation of the intermediates.

2. Related Arts

4-Oxo-1-benzopyran-2-carboxylic acid derivatives as final products of the invention are shown by the formula

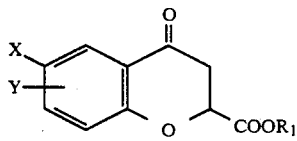
(I)

wherein X and Y are hydrogen atom, halogen atom or alkyl group, and $R_1$ is hydrogen atom or alkyl group.

The compounds represented by Formula I have been known as intermediates for preparing pharmacologically active compounds and more particularly the following optically active 6-fluoro-2,3-dihydro-2',5'-dioxo-spiro(4H-1-benzopyran-4',4'-imidazolidine)-2-carboxamide [Jap. Pat. No. 63-57588 (A) corresponding to a part of U.S. patent application Ser. No. 90,729 filed Aug. 28, 1987 and EP-A1-0264586] which shows powerful inhibition to activity of aldose reductase enzymes and thus have been expected as an effective ingredient for medicines to cure intractable complications due to diabetes.

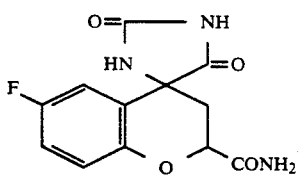
(VII)

The compounds shown by the Formula I, wherein $R_1$ is hydrogen atom have been disclosed in Jap. Pat. No. 63-250373 (A) corresponding to a part of said U.S. patent application Ser. No. 90,729 and EP-A1-0264586. According to disclosures given in the literatures, the compounds are synthesized as shown by following reaction formulae.

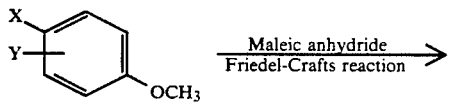

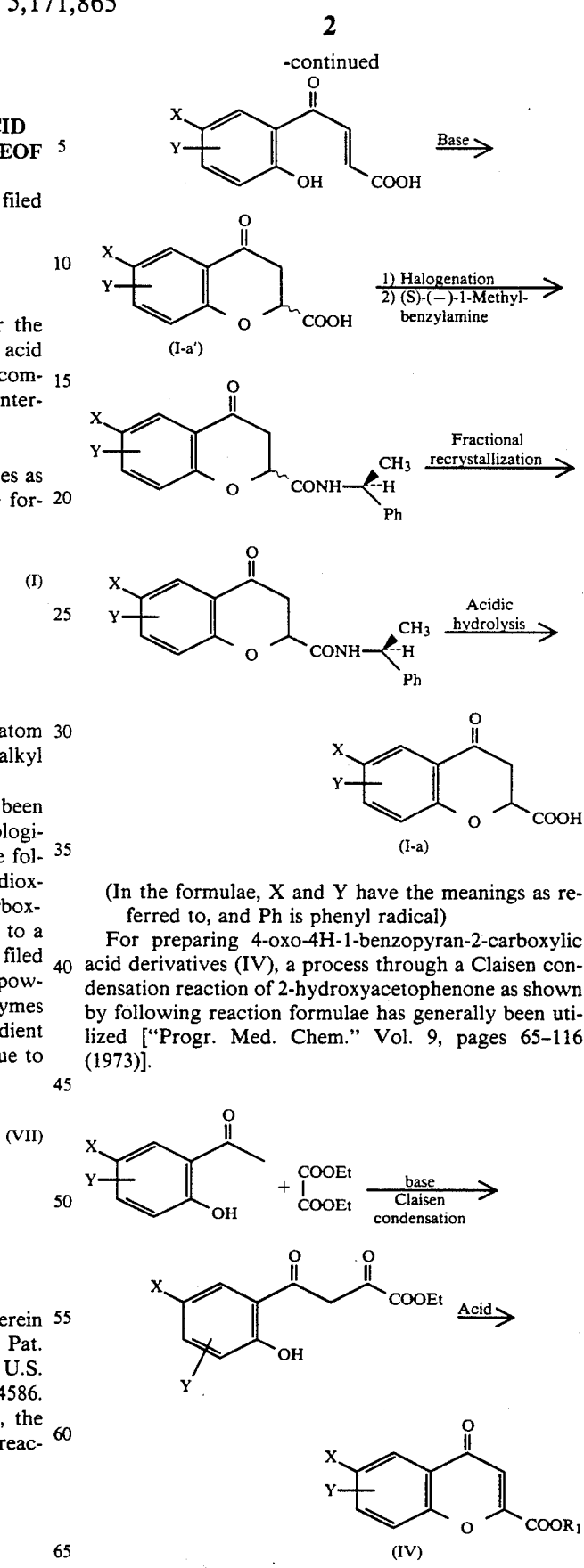

(In the formulae, X and Y have the meanings as referred to, and Ph is phenyl radical)

For preparing 4-oxo-4H-1-benzopyran-2-carboxylic acid derivatives (IV), a process through a Claisen condensation reaction of 2-hydroxyacetophenone as shown by following reaction formulae has generally been utilized ["Progr. Med. Chem." Vol. 9, pages 65–116 (1973)].

(In the formulae, X, Y and $R_1$ have the meanings as referred to, and Et is ethyl radical)

Further, a process for preparing 4-oxo-4H-1-benzo-pyran-2-carboxylic acid (IV-a), wherein phenoxyfumaric acid is subjected to ring closure reaction, in the presence of surfuric acid, as shown below has been disclosed in "Chem. Soc." Vol. 77, page 1179 (1900), but the literature does not refer to operation conditions and yield of the compound.

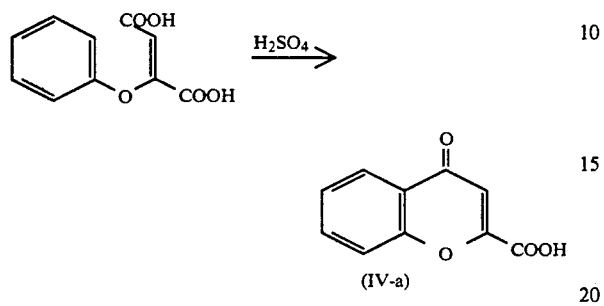

(IV-a)

Moreover, Jap. Pat. No. 60-132977 (A) discloses 6-fluoro-4-oxo-4H-1-benzopyran-2-carboxylic acid shown by the following formula (IV-b), but this literature does not show any process for synthesizing the compound.

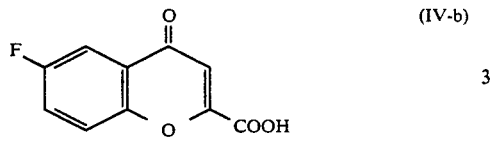

(IV-b)

Among the processes as referred to, the process proposed by the present inventors and disclosed in said Jap. Pat. No. 63-250373 (A) accompanies such an inconvinience in economical view point that (−)-isomer will also be prepared, in equimolecular amount, in addition to objective (+)-isomer, since the objective (+)-isomer can be prepared through an activation of the racemic 4-oxo-1-benzo-2-carboxylic acid derivative (I-a), reaction of the activated racemic compound with (S)-(−)-1-methylbenzylamine to prepare a diastereomer mixture of (S)-1-methylbenzylamides, and a optical resolution of the diastereomer mixture.

While, the process as disclosed in said "Progr. Med. Chem." Vol. 9, pages 65–116 (1973), which utilizes the Claisen condensation reaction, has such disadvantages from the view point of actual and industrial operation that anhydrous solvent is required and the raw material of 2-hydroxyacetophenone derivative is expensive.

SUMMARY OF THE INVENTION

A principal object of the invention is to provide a process for the preparation of optically active 4-oxo-1-benzopyran-2-carboxylic acid derivatives, which can be economically carried out to make an industrial production of the compounds possible.

An additional object of the invention is to provide an intermediate for synthesizing the desired derivatives.

Another object of the invention is to provide a process for the preparation of the intermediates.

The inventors have carefully and energetically studied and investigated for developing a novel process for preparing the compounds of optically active 4-oxo-1-benzopyran-2-carboxylic acid derivatives, from various view points and more particularly economical one inclusive of costs of raw materials and reagents as well as yield of the products, to finally find out a following synthetic route starting from a phenoxyfumaric acid derivative (VI) and terminating to the optically active 4-oxo-1-benzopyran-2-carboxylic acid derivative (I), whereby the invention has been established.

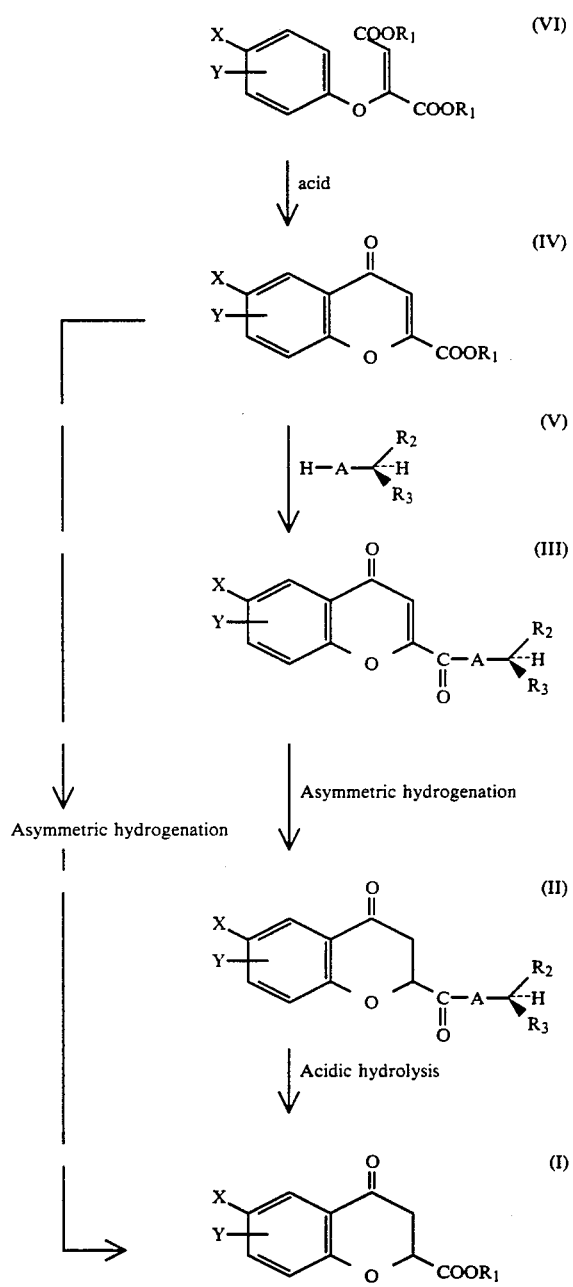

wherein X, Y and $R_1$ have the meanings as referred to, A is NH or O, $R_2$ is phenyl radical, substituted phenyl group or naphthyl radical, and $R_3$ is alkyl group or phenyl radical, but $R_2$ and $R_3$ do not mean the same radical of phenyl.

Basis of the invention lies in following findings.

It has been firstly elucidated that a ring closure of the starting phenoxyfumaric acid derivative (VI) under acidic condition provides 4-oxo-4H-1-benzopyran-2-carboxylic acid derivative (IV) with good yield.

When the compound (IV) is reacted with the optically active amine or alcohol (V) in a conventional manner for causing a condensation, the optically active compound (III) can be obtained. An asymmetric hydrogenation of the compound (III) provides a high diastereo selective reduction thereof to obtain the optically active compound (II) with good yield. Further, a hyrolysis of the compound (II) under an acidic condition provides the desired optically active derivative (I). Moreover, an asymmetric hydrogenation of the compound (IV) causes a high enantio selective reduction of the double bond to provide the desired optically active derivative (I) with good yield.

The phenoxyfumaric acid derivatives (VI) as the starting material in said synthetic route are novel but can be synthesized in the manner similar to a conventional process, for instance, as disclosed in "Indian J. CHem." Vol. 7, pages 971–976 (1969).

The ring closure reaction for converting the derivative (VI) into 4-oxo-4H-1-benzopyran-2-carboxylic acid derivative (IV) may be carried out in the presence of a suitable acid and without use any solvent. As the acid, concentrated sulfuric acid, polyphosphoric acid and the like are preferable and it is sufficient to use the acid by 1 to 10 equivalent amounts. There is no limitation on reaction temperature therefor and the reaction proceeds smoothly at a temperature of 10 to 100° C., and in this case, it requires 1 to 4 hours for completion of the reaction.

The conversion from the derivative (IV) into the optically active compound (III) can be carried out, as follows. In case of that $R_1$ is hydrogen atom (H), the compound (IV) is firstly made into the form of acid halide, for instance acid, chloride for activation thereof and then reacted with the optically active amine or alcohol (V) in the presence of a base and in a suitable solvent. The conversion into the acid chloride may be carried out in a conventional manner with use of a chlorinating agent, for instance thionyl chloride, phosphorous pentachloride or the like, which is used in 1 to 3 equivalent amounts. This activation reaction proceeds smoothly without use any solvent, but a solvent such as benzene, dichloromethane, dichloroethane or the like may be employed. There is no limitation on reaction temperature, but in general, a temperature of from 10° C. to a boiling point of the solvent is selected. The acid chloride can be quantitatively obtained, when the excess chlorinating agent is distilled out, after completion of the reaction. As the base for converting the acid chloride into the opticallyactive compound (III), triethylamine, pyridine and the like may be listed but triethylamine is preferable. As a solvent for this reaction, dichloromethane, dichloroethane, N,N-dimethylformamide or the like may be listed but dichloromethane is preferable. There is no limitation on reaction temperature, but in general, a temperature between 0° and 20° C. is selected. If the reaction temperature is set in the range, the reaction will be completed over about 1 hour.

While, in case of that the derivative or compound (IV) is an ester ($R_1$: alkyl group), the compound can be converted into the optically active compound (III) by reacting with equimolar amount of the optically active amine (V), in the presence of a base and in a suitable solvent. As the base for this reaction, it is preferable to use sodium methoxide, sodium ethoxide or the like which is employed in a trace amount (0.05 to 1.0 equivalent amount). As the solvent, benzene, toluene, diethylether may be listed but benzene is preferable. There is no limitation on reaction temperature, but in general, a temperature between 10° C. and boiling point of the solvent is selected. The necessary period of time for the reaction is 1 to 4 hours.

The optically active compound (II) can be obtained with a diastereo selectivity, by asymmetric reduction of the compound (III). Namely, the objective optically active (+)-isomer (III) can be obtained with a high selectivity, when an asymmetric hydrogenation is carried out on the double bond in the compound (II), by utilizing an asymmetric face selectivity to the asymmetric carbon atom introduced into the molecule. As a catalyst for the asymmetric hydrogenation, platinum oxide ($PtO_2$), platinum black, 5% platinum on activated carbon (5% Pt/C), palladium black, 5% palladium on activated carbon (5% Pd/C), rhodium oxide ($RhO_2$), Raney nickel or the like can be listed but plutinum oxide is preferable. There is no limitation on an amount of the catalyst, but it is preferable in an amount of about 1 to about 10%. As a solvent for the asymmetric hydrogenation, acetic acid, methanol, ethanol, ethyl acetate, benzene or the like may listed but acetic acid and methanol are preferable. There is no limitation on reaction pressure, but it is preferable to select the pressure in a range of 1 to about 30 kg/cm$^2$. There is no limitation also on reaction temperature, since the reaction proceeds smoothly at a temperature in a range of 10° to 100° C. When the temperature is of about 10° to 25° C., the reaction completes over 2 to 24 hours. The isolation of the objective optically active compound (II) can be carried out through a recrystallization or column chromatography.

The final objective compound of optically active 4-oxo-1-benzopyran-2-carboxylic acid derivative (I) can be obtained by subjecting the compound (II) to the acidic hydrolysis, As an acid therefor, hydrochloric acid, hydrobromic acid, sulfuric acid or the like mineral acid can be listed but it is preferable to use hydrochloric acid. As a solvent for the hydrolysis, methanol, ethanol, dioxane, acetic acid or the like can be listed but dioxane is more preferable. There is no limitation on reaction temperature. The period of time for the reaction is about 20 hours, when the temperature of 100° C. is selected. After the reaction, the objective compound (I) can be extracted with use of an organic solvent such as dichloromethane. An optical purity of the compound (I) shows more than 99% e.e.

As apparently seen from the synthetic route shown with the formulae, the compound (I) can also be directly obtained through symmetric hydrogenation of the compound (IV). In this case, an optically active phosphine-rhodium complex is employed, as catalyst. As the optically active phosphine for forming the complex, following (S,S)-DIOP (VIII-a), (S)-BINAP (VIII-b) or (S,S)-BPPM (VIII-c) is preferable.

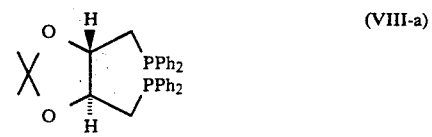

(VIII-a)

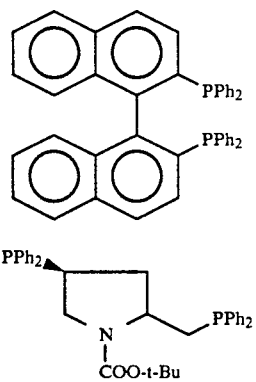

(VII-c)

wherein Ph has the meaning as referred to, and Bu is butyl radical.

There is no limitation on an amount of the catalyst but it is preferable to use the same in the amount of about 0.1-5 mmol %. It is preferable to use methanol, ethanol or the like as a solvent for the reaction. There is no limitation on reaction pressure but it is preferable to carry out the reaction under about 1 to 30 kg/cm². There is also no limitation on reaction temperature and the reaction proceeds smoothly at a temperature of 10°-100° C. The period of time for the reaction is 2 to 24 hours, when the temperature of 15°-20° C. is selected. An optical purity of the compound (I) in this route shows about 20% e.e., but can be increased to more than 99% e.e. through a refining step, for instance by repeating a fractional recrystallization, as disclosed in Jap. Pat. No. 63-250373 (A) referred to in the preamble of this specification.

For converting the final objective compound of 4-oxo-benzopyran-2-carboxylic acid derivative (I) into the optically active and pharmacologically active compound of 6-fluoro-2,3-dihydro-2',5'-dioxo-spiro(4H-1-benzopyran-4',4'-imidazolidine)-2-carboxamide (VIII), the compound (I) is thermally treated in the presence of sodium cyanate and ammonium carbonate to form hydantoin ring by utilizing so-called Bucherer synthesis, and the carboxyl radical at 2-position is converted into the amino radical according to a conventional manner.

PREFERRED EMBODIMENTS OF THE INVENTION

The invention will now be further explained with reference to Examples.

EXAMPLE 1

(Z)-Dimethyl 2-(4-fluorophenoxy)-2-butene-1,4-dioate

To a solution of 4-fluorophenol (22.4 g, 0.200 mol) and dimethyl acetylenedicarboxylate (28.4 g, 0.200 mol) in methanol (20 ml), triethylamine (1.00 g, 10.0 mmol) was added to stir the mixture for 1 hour at 10°-30° C.

The reaction mixture was cooled in an ice bath and resulting precipitate was obtained through a filtration, washed with a small amount of methanol, and dried in vacuo to afford 20.0 g (39.4%) of the desired compound as colorless crystals.

Further, the filtrate was concentrated and the residue was purified by silica gel column chromatography (CH$_2$Cl$_2$) to afford 16.0 g (45.3%) of the desired compound.

The desired compound totaled to 36.0 g (70.9%).

Melting point: 60°-61° C.

Mass spectrum (EI/DI) m/z: 254 (M+), 223 (M+-OMe), 195 (M+-COOMe, base peak).

IR spectrum ($\nu^{KBr}_{max}$) cm$^{-1}$: 1730 (COOMe), 1655 (C=C), 1505 (aromatic).

$^1$H-NMR spectrum (CDCl$_3$) δ ppm: 3.72 (3H, s, COOCH$_3$), 3.74 (3H, s, COOCH$_3$), 6.59 (1H, s, C=CH—), 6.9-7.0 (4H, m, Ar—H).

EXAMPLE 2

(Z)-2-(4-Fluorophenoxy)-2-butene-1,4-dicarboxylic acid

4N Sodium hydroxide solution (100 ml) was added to a solution of (Z)-dimethyl 2-(4-fluorophenoxy)-2-butene-1,4-dioate (25.4 g, 0.100 mol, obtained in Example 1) in methanol (100 ml), and the mixture was stirred for 3 hours at 25°-30° C.

The reaction mixture was concentrated in vacuo, acidified with conc.HCl, and cooled in an ice bath. The resulting precipitate was obtained through a filtration and recrystallized from methanol to afford 19.2 g (85.0%) of the desired compound as colorless crystals.

Melting point: 240°-245° C. (dec.)

Mass spectrum (EI/DI) m/z: 226 (M+), 181 (M+-COOH), 112 (base peak).

IR spectrum ($\nu^{KBr}_{max}$) cm$^{-1}$: 3400-2400 (OH), 1709 (COOH), 1600 (C=C), 1505 (aromatic).

$^1$H-NMR spectrum (DMSO-d$_6$) δ ppm: 6.54 (1H, s, C=CH—), 6.9-7.2 (4H, m, Ar—H).

EXAMPLE 3

Methyl 6-fluoro-4-oxo-4H-1-benzopyran-2-carboxylate (Z)-Dimethyl 2-(4-fluorophenoxy)-2-butene-1,4-dioate (2.54 g, 10,0 mmol, obtained in Example 1) was dissolved in conc.H$_2$SO$_4$ (4.0 ml) and the mixture was stirred for 4 hours at 25°-30° C.

The reaction mixture was poured into ice water and extracted with EtOAc (100 ml×3). Resulting extacts of organic layer were combined, washed with water, dried over Na$_2$SO$_4$, and concentrated in vacuo. The resulting crude product was recrystallized from methanol to afford 1.23 g (56.0%) of the desired compound as colorless crystals.

Melting point: 138°-139° C.

Mass spectrum (EI/DI) m/z: 222 (M+, base peak), 191 (M+-OMe), 163 (M+-COOMe).

IR spectrum ($\nu^{KBr}_{max}$) cm$^{-1}$: 1744 (COOMe), 1663 (C=O), 1623 (C=C), 1480 (aromatic).

$^1$H-NMR spectrum (CDCl$_3$) δ ppm: 4.03 (3H, s, COOCH$_3$), 7.11 (1H, s, C=CH—), 7.4-7.9 (3H, m, Ar—H).

EXAMPLE 4

Methyl 6-fluoro-4-oxo-4H-1-benzopyran-2-carboxylate (Z)-Dimethyl 2-(4-fluorophenoxy)-2-butene-1,4-dioate (2.54 g, 10,0 mmol, obtained in Example 1) was dissolved in polyphosphoric acid (10.0 ml) and the mixture was stirred for 1 hour at 80° C.

Then, 1.02 g (45.0%) of the desired compound was obtained by the similar procedure as in the case of Example 3.

Physical data of this compound were same with those given in Example 3.

EXAMPLE 5

6-Fluoro-4-oxo-4H-1-benzopyran-2-carboxylic acid (Z)-2-(4-Fluorophenoxy)-2-butene-1,4-dicarboxylic acid (10.0 g, 44.2 mmol, obtained in Example 2) was dissolved in conc.$H_2SO_4$ (20.0 ml) and the mixture was stirred for 30 minutes at 20°–40° C.

The reaction mixture was poured into ice water, and the resulting precipitate was obtained through a filtration, recrystallized from methanol to afford 8.64 g (93.9%) of the desired compound as colorless crystals.

Melting point: 261°–262° C.

Mass spectrum (EI/DI) m/z: 208 (M+, base peak).

IR spectrum ($\nu^{KBr}_{max}$) cm$^{-1}$: 3100–2400 (OH), 1736 (COOH), 1630 (C=O), 1589 (C=C), 1480 (aromatic).

$^1$H-NMR spectrum (DMSO-d$_6$) δ ppm: 6.90 (1H, s, C=CH—), 7.7–7.9 (3H, m, Ar—H).

EXAMPLE 6

6-Fluoro-4-oxo-4H-1-benzopyran-2-carboxylic acid (Z)-2-(4-fluorophenoxy)-2-butene-1,4-dicarboxylic acid (1.13 g, 10.0 mmol, obtained in Example 2) was dissolved in polyphosphoric acid (10.0 ml) and the mixture was stirred for 1 hour at 80° C.

Then, 950 mg (91.3%) of the desired compound was obtained by the similar procedure as in the case of Example 5.

Physical data of this compound were same with those given in Example 5.

EXAMPLE 7

(−)-N-[(R)-α-Methyl-p-chlorobenzyl]-6-fluoro-4-oxo-4H-1-benzopyran-2-carboxamide To a suspension of 6-fluoro-4-oxo-4H-1-benzopyran-2-carboxylic acid (1.0 g, 4.80 mmol, obtained in Example 5 or 6) in 1,2-dichloroethane (3.00 ml), thionyl chloride (571 mg, 4.80 mmol) was added at room temperature and the mixture was refluxed for 2 hours. The reaction mixture was concentrated in vacuo, and the residue was dissolved in $CH_2Cl_2$ (3.0 ml). The $CH_2Cl_2$ solution was added to a solution of (R)-α-methyl-p-chlorobenzylamine (748 mg, 4.80 mmol) and triethylamine (486 mg, 4.80 mmol) in $CH_2Cl_2$ (6.0 ml) under cooling in an ice bath over 1 hour, and the mixture was stirred at room temperature over one night.

The reaction mixture was washed with 5% HCl and water, dried over $Na_2SO_4$, concentrated in vacuo, and recrystallized from toluene to afford 1.58 g (95.0%) of the desired compound as colorless crystals.

Melting point: 132°–133° C.

Mass spectrum (EI/DI) m/z: 345 (M+, base peak).

IR spectrum ($\nu^{KBr}_{max}$) cm$^{-1}$: 1650 (C=C), 1657, 1677 (C=O).

$^1$H-NMR spectrum (CDCl$_3$) δ ppm: 1.65 (3H, d, J=6.8 Hz, —CH$_3$), 5.23–5.34 (1H, m, —CH—), 7.13 (1H, s, C=CH—), 7.13–7.84 (8H, m, CONH, Ar—H).

Elementary analysis: $C_{18}H_{13}ClFNO_3$ Cal.: C, 62.53; H, 3.79; N, 4.05; Found: C, 62.62; H, 3.80; N, 4.03.

$[\alpha]_D^{24}$: −28.5° (c=0.527, MeOH).

EXAMPLE 8

(−)-N-[(R)-α-Methyl-p-methylbenzyl]-6-fluoro-4-oxo-4H-1-benzopyran-2-carboxamide This compound was prepared by the similar procedure as in the case of Example 7, except for the treatment with (R)-α-methyl-p-methylbenzylamine (650 mg, 4.80 mmol) instead of (R)-α-methyl-p-chloro-benzylamine.

Then, 1.50 g (92.7%) of the desired compound were obtained as pale yellow powder.

Mass spectrum (EI/DI) m/z: 325 (M+).

IR spectrum ($\nu^{KBr}_{max}$) cm$^{-1}$: 1650 (C=C), 1657, 1677 (C=O).

$^1$H-NMR spectrum (CDCl$_3$) δ ppm: 1.65 (3H, d, J=6.8 Hz, —CH$_3$), 2.35 (3H, s, —CH$_3$), 5.23–5.34 (1H, m, —CH—), 7.08 (1H, d, J=7.8 Hz, CONH), 7.15 (1H, s, C=CH—), 7.18–7.85 (7H, m, Ar—H).

Elementary analysis: $C_{19}H_{16}FNO_3$ Cal.: C, 70.15; H, 4.96; N, 4.31; Found: C, 70.22; H, 4.85; N, 4.23.

$[\alpha]_D^{24}$: −13.5° (c=0.517, MeOH).

EXAMPLE 9

(−)-N-[(R)-α-Methylbenzyl]-6-fluoro-4-oxo-4H-1-benzopyran-2-carboxamide

This compound was prepared by the similar procedure as in the case of Example 7, except for the treatment with (R)-α-methylbenzylamine (582 mg, 4.80 mmol) instead of (R)-α-methyl-p-chloro-benzylamine.

The resulting clude product was recrystallized from EtOH to afford 1.22 g (81.3%) of the desired compound were obtained as a pale yellow powder.

Melting point: 127° C.

Mass spectrum (EI/DI) m/z: 311 (M+).

IR spectrum ($\nu^{KBr}_{max}$) cm$^{-1}$: 1657, 1677 (C=O).

$^1$H-NMR spectrum (CDCl$_3$) δ ppm: 1.66 (3H, d, J=6.8 Hz, —CH$_3$), 5.28–5.38 (1H, m, —CH—), 7.15 (1H, s, C=CH—), 7.15–7.84 (9H, m, CONH, Ar—H).

Elementary analysis: $C_{18}H_{14}FNO_3$ Cal.: C, 69.45; H, 4.53; N, 4.50; Found: C, 69.22; H, 4.41; N, 4.51.

$[\alpha]_D^{24}$: −35.3° (c=0.764, MeOH).

EXAMPLE 10

(−)-N-[(R)-α-Methylbenzyl]-6-fluoro-4-oxo-4H-1-benzopyran-2-carboxamide

Sodium methoxide (540 mg, 10.0 mmol) was added to a solution of methyl 6-fluoro-4-oxo-4H-1-benzopyran-2-carboxylate (2.22 g, 10.0 mmol, obtained in Example 3 or 4) and (R)-α-methylbenzylamine (1.21 g, 10.0 mmol) in dry benzene (20 ml) and the mixture was refluxed for 2 hours.

The reaction mixture was washed with water, dried over $Na_2SO_4$, and concentrated in vacuo. The residue was chromatographed on silica gel and eluted with $CH_2Cl_2$ to afford 1.90 g (61.1%) of the desired compound as colorless crystals.

Physical data of the compound were same with those given in Example 9.

EXAMPLE 11

(−)-N-[(R)-α-(n-Propyl)benzyl]-6-fluoro-4-oxo-4H-1-benzopyran-2-carboxamide

This compound was prepared by the similar procedure as in the case of Example 7, except for the treatment with (R)-α-(n-propyl)benzylamine (717 mg, 4.80 mmol) instead of (R)-α-methyl-p-chlorobenzylamine.

Then, 1.50 g (91.8%) of the desired compound were obtained as a pale yellow powder.

Mass spectrum (EI/DI) m/z: 339 (M+).

IR spectrum ($\nu^{KBr}_{max}$) cm$^{-1}$: 1657, 1677 (C=O).

$^1$H-NMR spectrum (CDCl$_3$) δ ppm: 0.97 (3H, t, J=7.3 Hz, —CH$_3$), 1.21–1.49 (2H, m, —CH$_2$—), 1.85–2.04 (2H, m, —CH$_2$—), 5.11–5.20 (1H, m, —CH—), 7.13 (1H, s, —CH=), 7.10–7.84 (8H, m, CONH, Ar—H).

Elementary analysis: $C_{20}H_{18}FNO_3$ Cal.: C, 70.78; H, 5.35; N, 4.13; Found: C, 70.75; H, 5.29; N, 4.20.

$[\alpha]_D^{24}$: −16.6° (c=1.02, MeOH).

EXAMPLE 12

(−)-N-[(R)-1-(α-Naphthyl)ethyl]-6-fluoro-4-oxo-4H-1-benzopyran-2-carboxamide

This compound was prepared by the similar procedure as in the case of Example 7, except for the treatment with (R)-1-(α-naphthyl)ethylamine (823 mg, 4.80 mmol) instead of (R)-α-methyl-p-chlorobenzylamine.

The resulting crude product was recrystallized from EtOH to afford 1.51 g (87.2%) of the desired compound as colorless crystals.

Melting point: 175° C.
Mass spectrum (EI/DI) m/z: 361 (M+).
IR spectrum ($\nu^{KBr}_{max}$) cm$^{-1}$: 1657, 1677 (C=O).
$^1$H-NMR spectrum (CDCl$_3$) δ ppm: 1.76 (3H, d, J=6.8 Hz, —CH$_3$), 5.96–6.07 (1H, m, —CH—), 7.13 (1H, s, C=CH—), 7.26–8.04 (11H, m, CONH, Ar—H).

Elementary analysis: $C_{22}H_{16}FNO_3$; Cal.: C, 73.12; H, 4.46; N, 3.86; Found: C, 73.14; H, 4.60; N, 3.69.

$[\alpha]_D^{24}$: −1.69° (c=0.591, CHCl$_3$).

EXAMPLE 13

N-[(R)-α-Methyl-p-methoxybenzyl]-6-fluoro-4-oxo-4H-1-benzopyran-2-carboxamide

This compound was prepared by the similar procedure as in the case of Example 7, except for the treatment with (R)-α-methyl-p-methoxybenzylamine (726 mg, 4.80 mmol) instead of (R)-α-methyl-p-chlorobenzylamine.

Then, 1.53 g (93.7%) of the desired compound were obtained as pale yellow powder.

Mass spectrum (EI/DI) m/z: 341 (M+).
IR spectrum ($\nu^{KBr}_{max}$) cm$^{-1}$: 1657, 1677 (C=O).
$^1$H-NMR spectrum (CDCl$_3$) δ ppm: 1.64 (3H, d, J=6.8 Hz, —CH$_3$), 3.80 (3H, s, —OCH$_3$), 5.23–5.34 (1H, m, —CH—), 7.14 (1H, s, C=CH—), Elementary analysis: $C_{19}H_{16}FNO_4$ Cal.: C, 66.86; H, 4.72; N, 4.10; Found: C, 66.75; H, 4.56; N, 4.04.

$[\alpha]_D^{24}$: ±0° (c=0.504, MeOH).

EXAMPLE 14

(−)-N-[(R)-α-Phenyl-p-chlorobenzyl]-6-fluoro-4-oxo-4H-1-benzopyran-2-carboxamide This compound was prepared by the similar procedure as in the case of Example 7, except for the treatment with (R)-α-phenyl-p-chlorobenzylamine (880 mg, 4.80 mmol) instead of (R)-α-methyl-p-chlorobenzylamine.

The resulting crude product was recrystallized from EtOH to afford 1.68 g (85.6%) of the desired compound as colorless crystals.

Melting point: 193° C.
Mass spectrum (EI/DI) m/z: 407 (M+).
IR spectrum ($\nu^{KBr}_{max}$) cm$^{-1}$: 1657, 1677 (C=O).
$^1$H-NMR spectrum (CDCl$_3$) δ ppm: 6.44 (1H, d, J=8.8 Hz, —CH—), 6.93 (1H, s, C=CH—), 7.31–7.92 (12H, m, Ar—H), 9.93 (1H, d, J=8.8 Hz, CONH).

Elementary analysis: $C_{23}H_{15}ClFNO_3$ Cal.: C, 67.73; H, 3.71; N, 3.43; Found: C, 67.71; H, 3.68; N, 3.37.

$[\alpha]_D^{24}$: −12.8° (c=0.570, DMF).

EXAMPLE 15

(−)-(R)-α-Methylbenzyl 6-fluoro-4-oxo-4H-1-benzopyran-2-carboxylate

This compound was prepared by the similar procedure as in the case of Example 7, except for the treatment with (R)-α-methylbenzyl alcohol (587 mg, 4.80 mmol) instead of (R)-α-methyl-p-chlorbenzylamine.

Then, 1.43 g (95.0%) of the desired compound was obtained as pale yellow and viscous oil.

Mass spectrum (EI/DI) m/z: 312 (M+).
IR spectrum ($\nu^{KBr}_{max}$) cm$^{-1}$: 1744, 1664 (C=O).
$^1$H-NMR spectrum (CDCl$_3$) δ ppm: 1.72 (3H, d, J=6.8 Hz, —CH$_3$), 6.15 (1H, q, J=6.8 Hz, —CH$_2$—), 7.14 (1H, s, C=CH—), 7.26–7.84 (8H, m, Ar—H), Elementary analysis: $C_{18}H_{13}FNO_4$; Cal.: C, 69.23; H, 4.20; N, 4.49; Found: C, 69.14; H, 4.41; N, 4.59.

$[\alpha]_D^{24}$: −45.9° (c=1.02, MeOH).

EXAMPLE 16

(+)-N-[(R)-α-Methyl-p-chlorobenzyl]-6-fluoro-3,4-dihydro-4-oxo-2H-1-benzopyran-2-carboxamide Platinum oxide (50 mg, 0.220 mmol) was added to a solution of (−)-N-[(R)-α-methyl-p-chlorobenzyl]-6-fluoro-4-oxo-4H-1-benzopyran-2-carboxamide (1.00 g, 2.89 mmol, obtained in Example 7) in acetic acid (20 ml), and the mixture was hydrogenated at 20° C. under H$_2$ (4 kg/cm$^2$) with stirring for 18 hours. It was determined that the (+)-isomer/(−)-isomer ratio of the reduction product was 4.1/1 (61% d.e.) by $^1$H-NMR analysis.

The catalyst was filtered off and the filtrate was concentrated in vacuo. The residue was purified by silica gel column chromatography (20% EtOAc/benzene) to afford 728 mg (72.4%) of of the desired compound having following physical data, as colorless crystals, and 177 mg (17.6%) of a diastereomer thereof, namely (−)-N-[(R)-α-Methyl-p-chlorobenzyl]-6-fluoro-3,4-dihydro-4-oxo-2H-1-benzopyran-2-carboxamide.

Melting point: 159° C.
Mass spectrum (EI/DI) m/z: 347 (M+).
IR spectrum ($\nu^{KBr}_{max}$) cm$^{-1}$: 1695, 1660 (C=O).
$^1$H-NMR spectrum (CDCl$_3$) δ ppm: 1.60 (3H, d, J=7.3 Hz, —CH$_3$), 2.83 (1H, dd, J=17.1, 12.7 Hz, —CH$_2$—, Hax), 3.14 (1H, dd, J=17.1, 3.4 Hz, —CH$_2$—, Heq), 4.93 (1H, dd, J=12.7, 3.4 Hz, —CH—), 5.11–5.22 (1H, m, —CH—), 6.82–7.58 (8H, m, CONH, Ar—H).

Elementary analysis: $C_{18}H_{15}ClFNO_3$ Cal.: C, 62.17; H, 4.35; N, 4.03; Found: C, 62.45; H, 4.23; N, 4.02.

$[\alpha]_D^{24}$: +108° (c=0.535, MeOH).

EXAMPLE 17

(+)-N-[(R)-α-Methyl-p-methylbenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-methyl-p-methylbenzyl]-6-fluoro-4-oxo-4H-1-benzopyran-2-carboxamide (1.00 g, 3.07 mmol, obtained in Example 8) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 3.1/1 (51% d.e.) by $^1$H-NMR analysis.

Then, 662 mg (65.8%) of the desired compound was obtained as colorless crystals.

Melting point: 157° C.

Mass spectrum (EI/DI) m/z: 327 (M+).

IR spectrum ($\nu^{KBr}_{max}$) cm$^{-1}$: 1695, 1667 (C=O).

$^1$H-NMR spectrum (CDCl$_3$) δ ppm: 1.59 (3H, d, J=7.3 Hz, —CH$_3$), 2.35 (3H, s, —CH$_3$), 2.87 (1H, dd, J=17.1, 12.7 Hz, —CH$_2$—, Hax), 3.17 (1H, dd, J=17.1, 3.4 Hz, —CH$_2$—, Heq), 4.93 (1H, dd, J=12.7, 3.4 Hz, —CH—), 5.13–5.24 (1H, m, —CH—), 6.87–7.59 (8H, m, CONH, Ar—H).

Elementary analysis: C$_{19}$H$_{18}$FNO$_3$ Cal.: C, 69.71; H, 5.54; N, 4.28; Found: C, 69.45; H, 5.43; N, 4.12.

[α]$_D^{24}$: +117° (c=0.515, MeOH).

EXAMPLE 18

(+)-N-[(R)-α-Methylbenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-methylbenzyl]-6-fluoro-4-oxo-4H-1-benzopyran-2-carboxamide (1.00 g, 3.21 mmol, obtained in Example 9) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 2.9/1 (49% d.e.) by $^1$H-NMR analysis.

Then, 670 mg (66.6%) of the desired compound was obtained as colorless crystals.

Melting point: 140° C.

Mass spectrum (EI/DI) m/z: 313 (M+).

IR spectrum ($\nu^{KBr}_{max}$) cm$^{-1}$: 1695, 1666 (C=O).

$^1$H-NMR spectrum (CDCl$_3$) δ ppm: 1.59 (3H, d, J=17.6 Hz, —CH$_3$), 2.76–2.93 (1H, m, —CH$_2$—, Hax), 3.05–3.24 (1H, m, —CH$_2$—, Heq), 4.85–5.18 (1H, m, —CH—), 6.84–7.59 (9H, m, CONH, Ar—H).

Elementary analysis: C$_{18}$H$_{16}$FNO$_3$ Cal.: C, 69.00; H, 5.15; N, 4.47; Found: C, 69.15; H, 5.29; N, 4.22.

[α]$_D^{24}$: +105° (c=0.526, MeOH).

EXAMPLE 19

(+)-N-[(R)-α-(n-Propyl)benzyl]-6-fluoro-3,4-dihydro-4-oxo-2H-1-benzopyran-2-carboxamide This compound was prepared by the similar procedure as in the case of Example 16, except for the treatment with (−)-N-[(R)-α-(n-propyl)-benzyl]-6-fluoro-4-oxo-4H-1-benzopyran-2-carboxamide (1.00 g, 2.95 mmol, obtained in Example 11) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 2.5/1 (43% d.e.) by $^1$H-NMR analysis.

Then, 663 mg (65.9%) of the desired compound was obtained as colorless crystals.

Melting point: 138° C.

Mass spectrum (EI/DI) m/z: 341 (M+).

IR spectrum ($\nu^{KBr}_{max}$) cm$^{-1}$: 1695, 1666 (C=O).

$^1$H-NMR spectrum (CDCl$_3$) δ ppm: 0.96 (3H, t, J=7.3 Hz, —CH$_3$), 1.24–1.92 (4H, m, —CH$_2$—), 2.82 (1H, dd, J=17.6, 12.7 Hz, —CH$_2$—, Hax), 3.14 (1H, dd, J=17.6, 3.4 Hz, —CH$_2$—, Heq), 4.93 (1H, dd, J=12.7, 3.4 Hz, —CH—), 4.99–5.08 (1H, m, —CH—), 6.81 (1H, d, J=8.3 Hz, CONH), 7.05–7.57 (8H, m, Ar—H).

Elementary analysis: C$_{20}$H$_{20}$FNO$_3$; Cal.: C, 61.25; H, 5.14; N, 3.57; Found: C, 61.41; H, 5.29; N, 3.42.

[α]$_D^{24}$: +87.0° (c=0.540, MeOH).

EXAMPLE 20

(+)-N-[(R)-1-(α-Naphthyl)ethyl]-6-fluoro-3,4-dihydro-4-oxo-2H-1-benzopyran-2-carboxamide This compound was prepared by the similar procedure as in the case of Example 16, except for the treatment with (−)-N-[(R)-1-(α--naphthyl)ethyl]-6-fluoro-4-oxo-4H-1-benzopyran-2-carboxamide (1.00 g, 2.77 mmol, obtained in Example 12) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 2.3/1 (39% d.e.) by $^1$H-NMR analysis.

Then, 645 mg (64.1%) of the desired compound was obtained as colorless crystals.

Melting point: 190° C.

Mass spectrum (EI/DI) m/z: 363 (M+).

IR spectrum ($\nu^{KBr}_{max}$) cm$^{-1}$: 1695, 1666 (C=O).

$^1$H-NMR spectrum (CDCl$_3$) δ ppm: 1.75 (3H, d, J=6.8 Hz, —CH$_3$), 2.82 (1H, dd, J=17.1, 11.7 Hz, —CH$_2$—, Hax), 3.17 (1H, dd, J=17.1, 3.4 Hz, —CH$_2$—, Heq), 4.95 (1H, dd, J=11.7, 3.4 Hz, —CH—), 5.91–6.03 (1H, m, —CH—), 6.73–7.97 (11H, m, CONH, Ar—H).

Elementary analysis: C$_{22}$H$_{18}$FNO$_3$; Cal.: C, 72.72; H, 4.99; N, 3.85; Found: C, 72.51; H, 5.00; N, 3.82.

[α]$_D^{24}$: +17.7° (c=0.509, CHCl$_3$).

EXAMPLE 21

(+)-N-[(R)-α-Methyl-p-methoxybenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-methyl-p-methoxybenzyl]-6-fluoro-4-oxo-4H-1-benzopyran-2-carboxamide (1.00 g, 3.21 mmol, obtained in Example 13) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 1.4/1 (17% d.e.) by $^1$H-NMR analysis.

Then, 520 mg (51.7%) of the desired compound was obtained as colorless crystals.

Melting point: 145° C.

Mass spectrum (EI/DI) m/z: 343 (M+).

IR spectrum ($\nu^{KBr}_{max}$) cm$^{-1}$: 1695, 1668 (C=O).

$^1$H-NMR spectrum (CDCl$_3$) δ ppm: 1.57 (3H, d, J=6.8 Hz, —CH$_3$), 2.84 (1H, dd, J=17.1, 12.7 Hz, —CH$_2$—, Hax), 3.16 (1H, dd, J=17.1, 3.4 Hz, —CH$_2$—, Heq), 3.79 (3H, s, —OCH$_3$), 4.91 (1H, dd, J=12.7, 3.4 Hz, —CH—), 5.13–5.18 (1H, m, —CH—), 6,81–7.84 (8H, m, CONH, Ar—H).

Elementary analysis: C$_{19}$H$_{18}$FNO$_4$; Cal.: C, 66.66; H, 5.30; N, 4.09; Found: C, 66.71; H, 5.29; N, 4.12.

[α]$_D^{24}$: +113° (c=0.502, MeOH).

EXAMPLE 22

(+)-N-[(R)-α-Phenyl-p-chlorobenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-phenyl-p-chlorobenzyl]-6-fluoro-4oxo-4H-1-benzopyran-2-carboxamide (1.00 g, 2.45 mmol, obtained in Example 13) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 1.1/1 (5% d.e.) by $^1$H-NMR analysis.

Then, 473 mg (47.1%) of the desired compound was obtained as colorless crystals.

Melting point: 167° C.
Mass spectrum (EI/DI) m/z: 409 (M+).
IR spectrum ($\nu^{KBr}_{max}$) cm$^{-1}$: 1695, 1665 (C=O).
$^1$H-NMR spectrum (CDCl$_3$) δ ppm: 2.92 (1H, dd, J=17.1, 12.2 Hz, —CH$_2$—, Hax), 3.18 (1H, dd, J=17.1, 3.9 Hz, —CH$_2$—, Heq), 4.93 (1H, dd, J=12.2, 3,9 Hz, —CH—). 6.27 (1H, d, J=8.3 Hz, —CH—), 7.03-7.59 (13H, m, CONH, Ar—H).
Elementary analysis: C$_{23}$H$_{17}$ClFNO$_3$; Cal.: C, 67.41; H, 4.18; N, 3.42; Found: C, 67.41; H, 4.29; N, 3.42.
$[\alpha]_D^{24}$: +81.4° (c=0.553, MeOH).

EXAMPLE 23

(+)-(R)-α-Methylbenzyl 6-fluoro-3,4-dihydro-4-oxo-2H-1-benzopyran-2-carboxylate

This compound was prepared by the similar procedure as in the case of Example 16, except for the treatment with (−)-(R)-α-methylbenzyl 6-fluoro-4-oxo-4H-1-benzopyran-2-carboxylate (1.00 g, 3.20 mmol, obtained in Example 15) instead of (−)-N-[(R)-α-methyl-p-chlorobenzyl]-6-fluoro-4-oxo-4H-1-benzopyran-2-carboxamide. It was determined that the (+)-isomer/(−)-isomer ratio of the reduction product was 1.4/1 (17% d.e.) by $^1$H-NMR analysis.

Then, 499 mg (49.6%) of the desired compound was obtained as colorless crystals.

Melting point: 98° C.
Mass spectrum (EI/DI) m/z: 314 (M+).
IR spectrum ($\nu^{KBr}_{max}$) cm$^{-1}$: 1735, 1692 (C=O).
$^1$H-NMR spectrum (CDCl$_3$) δ ppm: 1.57 (3H, d, J=6.8 Hz, —CH$_3$), 3.09 (1H, d, J=7.8 Hz, —CH$_2$—, Hax), 3.08 (1H, d, J=5.9 Hz, —CH$_2$—, Heq), 5.08 (1H, dd, J=7.8, 5.9 Hz, —CH—), 5.96 (1H, q, J=6.8 Hz, —CH—), 7.05-7.52 (8H, m, Ar—H).
Elementary analysis: C$_{18}$H$_{15}$FNO$_4$; Cal.: C, 68.78; H, 4.81; N, 4.46; Found: C, 68.62; H, 4.80; N, 4.43.
$[\alpha]_D^{24}$: +129° (c=1.01, MeOH).

EXAMPLE 24

(+)-N-[(R)-α-Methylbenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-methylbenzyl]-6-fluoro-4-oxo-4H-1-benzopyran-2-carboxamide (1.00 g, 3.21 mmol, obtained in Example 9 or 10) instead of (−)-N-[(R)-α-methyl-p-chlorobenzyl]-6-fluoro-4-oxo-4H-1-benzopyran-2-carboxamide and 5% plutinum on activated carbon instead of platinum oxide. It was determined that the (+)-isomer/(−)-isomer ratio of the reduction product was 1.1/1 (5% d.e.) by $^1$H-NMR analysis.

Then, 469 mg (46.6%) of the desired compound was obtained as colorless crystals.

Physical data of the compound were same with those given in Example 18.

EXAMPLE 25

(+)-N-[(R)-α-Methylbenzyl]-6-fluoro-3,4-dihydro-4-oxo-2H-1-benzopyran-2-carboxamide Raney nickel (100 mg) was added to a solution of (−)-N-[(R)-α-methylbenzyl]-6-fluoro-4-oxo-4H-1-benzopyran-2-carboxamide (1.00 g, 3.21 mmol, obtained in Example 9 or 10) in ethanol (20 ml) and the mixture was hydrogenated for 1 hour at a temperature of 55°-60° C. under H$_2$ atomosphere (1 kg/cm$^2$) with stirring. It was determined that the (+)-isomer/(−)-isomer ratio of the reduction product was 1.4/1 (26% d.e.) by $^1$H-NMR analysis.

The catalyst was filtered off and the filtrate was concentrated in vacuo. The residue was purified by silica gel column chromatography (20% EtOAc/benzene) to afford 469 mg (46.6%) of the desired compound as colorless crystals.

Physical data of the compound were same with those given in Example 18.

EXAMPLE 26

(+)-6-fluoro-3,4-dihydro-4-oxo-2H-1-benzopyran-2-carboxylic acid (+)-2,3-O-isopropyliden-2,3-dihydroxy-1,4-bis(diphenylphosphyno)butane (120 mg, 0.0240 mmol) was added to a solution of dichloro-bis-[(1,3)-cyclooctadiene]-dirhodium(I) (59.2 mg, 0.0120 mmol) in dry benzene (0.5 ml) under argon atmosphere and the mixture was stirred for 15 minutes to prepare an optical active rhodium catalyst. The benzene solution (catalyst) was added to a suspension of 6-fluoro-4-oxo-4H-1-benzopyran-2-carboxylic acid (1.00 g, 4.80 mmol, obtained in Example 5) in methanol (30 ml) under argon atmosphere. Gaseous phase was changed for H$_2$, and the mixture was stirred for 24 hours under H$_2$ (4 kg/cm$^2$) at 40° C.

The mixture was concentrated in vacuo, the residue was suspended in saturated aqueous NaHCO$_3$. Insoluble materials therein were filtered off, and the filtrate was acidified to pH 1 with conc.HCl. The resulting precipitate was obtained through filtration, washed with water, and dried to afford the desired compound as colorless crystals.

It was determined that optical purity of the compound was 19% e.e. by the specific rotation.

Melting point: 178° C.
Mass spectrum (EI/DI) m/z: 210 (M+).
$^1$H-NMR spectrum (CDCl$_3$) δ ppm: 2.99 (1H, dd, J=17.1, 7.3 Hz, —CH$_2$—, Hax), 3.13 (1H, dd, J=17.1, 5.3 Hz, —CH$_2$—, Heq), 5.35 (1H, dd, J=7.3, 5.3 Hz, —CH—), 7.16-7.53 (3H, m, Ar—H).
$[\alpha]_D^{24}$: +16.0° (c=0.624, DMF).
Reference data (Standard Sample), $[\alpha]_D^{24}$: +83.0° (c=1.00, DMF).

EXAMPLE 27

(+)-N-[(R)-α-Methyl-p-chlorobenzyl]-6-fluoro-3,4-dihydro-4-oxo-2H-1-benzopyran-2-carboxamide Raney nickel (400 mg) was added to a solution of (−)-N-[(R)-α-methyl-p-chlorobenzyl]-6-fluoro-4-oxo-4H-1-benzopyran-2-carboxamide (1.00 g, 2.89 mmol, obtained in Example 7) in ethanol (20 ml) and the mixture was hydrogenated for 5 hour at a temperature of 55°-60° C. under H$_2$ atomosphere (4 kg/cm$^2$) with stirring. It was determined that the (+)-isomer/(−)-isomer ratio of the reduction product was 2.7/1 (46% d.e.) by $^1$H-NMR analysis.

The catalyst was filtered off and the filtrate was concentrated in vacuo. The residue was purified by silica gel column chromatography (20% EtOAc/benzene) to afford 710 mg (70.6%) of the desired compound as colorless crystals.

Physical data of the compound were same with those given in Example 16.

EXAMPLE 28

(−)-N-[(R)-α-Methyl-p-bromobenzyl]-6-fluoro-4-oxo-4H-1-benzopyran-2-carboxamide

This compound was prepared by the similar procedure as in the case of Example 7, except for the treatment with (R)-α-methyl-p-bromobenzylamine (960 mg, 4.80 mmol) instead of (R)-α-methyl-p-chlorobenzylamine.

The resulting crude product was recrystallized from EtOH to afford 1.70 g (91.0%) of the desired compound as colorless crystals.

Melting point: 142° C.

Mass spectrum (EI/DI) m/z: 390 (M+).

IR spectrum ($\nu^{KBr}_{max}$) cm$^{-1}$: 1650 (C=C), 1657, 1677 (C=O).

$^1$H-NMR spectrum (CDCl$_3$) δ ppm: 1.65 (3H, d, J=6.8 Hz, —CH$_3$), 5.22–5.33 (1H, m, —CH—), 7.06 (1H, d, J=7.8 Hz, —CONH), 7.14 (1H, s, —CH=), 7.27–7.85 (7H, m, Ar—H).

Elementary analysis: C$_{18}$H$_{13}$BrFNO$_3$; Cal.: C, 55.41; H, 3.36; N, 3.59; Found: C, 55.22; H, 3.60; N, 4.03.

$[\alpha]_D^{24}$: −29.5° (c=0.505, MeOH).

EXAMPLE 29

(+)-N-[(R)-α-Methyl-p-bromobenzyl]-6-fluoro-3,4-dihydro-4-oxo-2H-1-benzopyran-2-carboxamide This compound was prepared by the similar procedure as in the case of Example 16, except for the treatment with (−)-N-[(R)-α-methyl-p-bromobenzyl]-6-fluoro-4-oxo-4H-1-benzopyran-2-carboxamide (1.00 g, 2.56 mmol) instead of (−)-N-[(R)-α-methyl-p-chlorobenzyl]-6-fluoro-4-oxo-4H-1-benzopyran-2carboxamide. It was determined that the (+)-isomer/(−)-isomer ratio of the reduction product was 3.3/1 (53% d.e.) by $^1$H-NMR analysis.

Melting point: 153° C.

Mass spectrum (EI/DI) m/z: 392 (M+).

IR spectrum ($\nu^{KBr}_{max}$) cm$^{-1}$: 1695, 1667 (C=O).

$^1$H-NMR spectrum (CDCl$_3$) δ ppm: 1.57 (3H, d, J=6.8 Hz, —CH$_3$), 2.84 (1H, dd, J=17.1, 12.7 Hz, —CH$_2$—, Hax), 3.16 (1H, dd, J=17.1, 3.4 Hz, —CH$_2$—, Heq), 4.92 (1H, dd, J=12.7, 3.4 Hz, —CH), 5.10–5.20 (1H, m, —CH—), 6.78 (1H, d, J=7.8 Hz, —CONH), 7.03–7.59 (7H, m, Ar—H).

Elementary analysis: C$_{18}$H$_{15}$BrFNO$_3$; Cal.: C, 55.12; H, 3.85; N, 3.57; Found: C, 55.40; H, 3.63; N, 3.32.

$[\alpha]_D^{24}$: +112° (c=0.500, MeOH).

EXAMPLE 30

(+)-N-[(R)-α-Methyl-p-bromobenzyl]-6-fluoro-3,4-dihydro-4-oxo-2H-1-benzopyran-2-carboxamide Raney nickel (500 mg) was added to a solution of (−)-N-[(R)-α-methyl-p-bromobenzyl]-6-fluoro-4-oxo-4H-1-benzopyran-2-carboxamide (1.00 g, 2.56 mmol, obtained in Example 28) in ethanol (20 ml) and the mixture was hydrogenated for 24 hour at a temperature of 55°–60° C. under H$_2$ atmosphere (4 kg/cm$^2$) with stirring. It was determined that the (+)-isomer/(−)-isomer ratio of the reduction product was 2.0/1 (33%d.e.) by $^1$H-NMR analysis.

The catalyst was filtered off and the filtrate was concentrated in vacuo. The residue was purified by silica gel column chromatography to afford 650 mg (64.7%) of the desired compound as colorless crystals.

Physical data of the compound were same with those given in Example 29.

What is claimed is:

1. An optically active compound of the formula

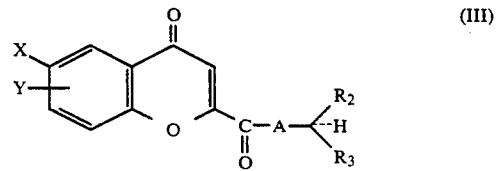

(III)

wherein A is NH or O, X and Y are hydrogen atoms, halogen atoms or alkyl groups, R$_2$ is a phenyl radical, which may be substituted by a member selected from the group consisting of halogen, alkyl having 1 to 3 carbon atoms or alkoxy having 1 to 3 carbon atoms, or a naphthyl radical, and R$_3$ is an alkyl group or a phenyl radical, but R$_2$ and R$_3$ are not the same phenyl radical.

2. An optically active compound of the formula

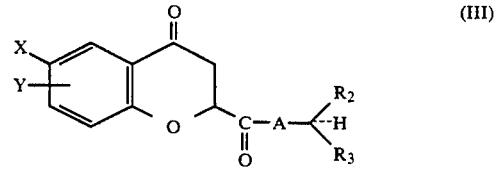

(III)

wherein A is NH or O, X and Y are hydrogen atoms, halogen atoms or alkyl groups, R$_2$ is a phenyl radical, which may be substituted by a member selected from the group consisting of halogen, alkyl having 1 to 3 carbon atoms or alkoxy having 1 to 3 carbon atoms, or a naphthyl radical, and R$_3$ is an alkyl group or a phenyl radical, but R$_2$ and R$_3$ are not the same phenyl radical.

* * * * *